United States Patent [19]

Ishibai et al.

[11] 3,951,721
[45] Apr. 20, 1976

[54] METHOD OF FORMING A MECHANICALLY STRONG REFLECTIVE SURFACE

[75] Inventors: Mutuo Ishibai, Hachioji; Kunizo Hosino, Kokubunji, both of Japan

[73] Assignee: Hitachi, Ltd., Japan

[22] Filed: Apr. 18, 1972

[21] Appl. No.: 245,123

[30] Foreign Application Priority Data

Apr. 21, 1971 Japan.............................. 46-25242

[52] U.S. Cl................................ 156/154; 427/162; 156/280; 156/330; 428/285; 428/286; 428/416; 250/228; 356/236; 356/243
[51] Int. Cl.......................... B32b 31/22; G01j 1/04
[58] Field of Search ............ 356/236, 243; 250/228; 156/280, 330; 117/35 R, 159; 161/3.5, 4, 89, 186, 94, 95, 184, 185, 92, 93

[56] References Cited
UNITED STATES PATENTS

| | | | |
|---|---|---|---|
| 2,278,345 | 3/1942 | Benson | 156/280 |
| 2,653,118 | 9/1953 | Seymour | 161/93 |
| 3,216,848 | 11/1965 | Hart et al. | 161/186 |
| 3,284,262 | 11/1966 | Dowling | 156/280 |
| 3,349,665 | 10/1967 | Grosheim et al. | 356/236 |
| 3,512,895 | 5/1970 | Grum et al. | 356/243 |

OTHER PUBLICATIONS

Madden, John J., "Epoxy Resins" Modern Plastics Encyclopedia, Vol. 46, No. 10A, Oct. 1969, McGraw-Hill Publications, pp. 123-124.

Primary Examiner—William J. Van Balen
Assistant Examiner—Charles E. Lipsey
Attorney, Agent, or Firm—Craig & Antonelli

[57] ABSTRACT

A reflecting surface is formed on an inner base plate of an integrating sphere. A fabric is bonded to an under coat layer of said base plate and furthermore a reflecting layer is formed on said fabric. As the fabric, cheese cloth is used and said reflecting layer comprises barium sulfate and polyvinyl alcohol.

20 Claims, 2 Drawing Figures

METHOD OF FORMING A MECHANICALLY STRONG REFLECTIVE SURFACE

BACKGROUND OF THE INVENTION

1. Field of the Invention

The present invention relates to a reflecting surface of photometer, colourmeter and the like, a reflecting surface widely usable as a working white standard and a method for producing the surface.

2. Description of the Prior Art

Conventionally, MgO smoked surface has often been used as a working standard for spectral reflectance in spectromesuring, spectrophotometer, etc. Said MgO smoked surface has excellent spectrophotomeric characteristics such as a high spectral reflectance of the smoked surface, low selectivity of wavelength in visible area and similarity to the perfect diffusing surface.

However, the MgO smoked surface has extremely low mechanical strength, lacks durability and has great limitation in its production.

Many attempts have been made to obtain a working white standard to be substituted for said MgO smoked surface, and a white coating surface obtained by spray coating method has been generally utilized in case of a large reflecting surface such as integrating sphere. The reflecting surface according to said method is obtained by repeatedly spraying a purified white paint onto a previously under coated surface to laminate the coating layers until a certain spectral reflectance and diffusibility are attained.

Such coating layer has relatively higher mechanical strength than the MgO smoked surface and can be used as a working reflecting surface. However, optical characteristics corresponding to those of the smoked surface can be obtained only with difficulty and only over a long period of time.

For example, at least 1 mm thickness of the coating layer is required to obtain a spectral reflectance of higher than 95% in visible area (relative value to the MgO smoked surface). However, as many as 30 – 40 spraying applications are required in view of the conditions of spray coating and the paint compositions and a considerably long coating period is necessary when drying time and the like are included. Furthermore, in many cases, the surface of the coating layer becomes rough or cracks are formed thereon, whereby the spectral reflectance and diffusibility are damaged. Furthermore, such coating layer changes with lapse of time due to temperature, humidity, radiation, dusts, etc. and it is difficult to maintain the original characteristics for a long period. Therefore, re-coating is necessary at regular intervals (generally, one time in 1 – 3 years) depending upon extent of deterioration.

A second problem is the trouble of dusts and loss of paint caused by spray coating.

Dispersion of paint in a large amount in the air during spray coating results in economical loss and contamination of air. Furthermore, it causes serious trouble to painters, other persons and to buildings, equipment, and so forth in which and around which the spray coating operation is accomplished. These troubles are especially serious in such coating conditions as in an integrating sphere. Therefore, extra exhaust apparatus and dust preventing equipment are required. Furthermore, during the coating, the surrounding buildings and equipment must be closed and in many cases, the usual business is prevented.

SUMMARY OF THE INVENTION

The object of the present invention is to remove said defects and provide a reflecting surface having excellent reflectance.

Another object of the present invention is to provide a reflecting surface having a high mechanical strength and shock resistance and a stable physical properties against changes in temperature.

Further object of the present invention is to provide a method for coating a reflecting surface according to which dispersion of paint during coating is prevented and evil influence due to dusts can be overcome.

The above objects can be attained by the present invention which is characterized in that a fabric is bonded to an under coat layer on a base plate which is to be coated and a given reflecting layer is formed on said fabric.

DESCRIPTION OF THE PREFERRED EMBODIMENTS

Figure 1:
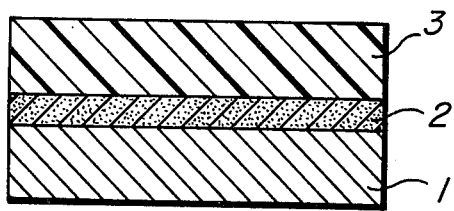
FIG. 1 shows a cross section of the conventional reflecting surface.
Figure 2:
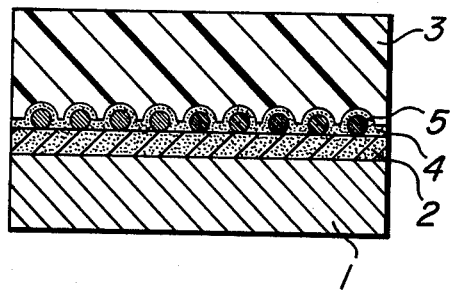
FIG. 2 shows a cross section of one embodiment of the present invention.

FIG. 1 shows the structure of the conventional reflecting surface, wherein 1 is an inner base plate of a photometer and the like, 2 is an under coat layer and 3 is a reflecting layer (finish coat layer). On the other hand, as shown in FIG. 2, the reflecting surface of the present invention is obtained by bonding fabric 5 such as cheese cloth to the surface of under coat layer 2 on rust proofed base plate 1 with adhesive 4, then coating thereto repeatedly several times a purified pasty white paint having a certain viscosity, drying the paint and thereafter spraying to the surface of the coating layer a white paint in extremely thin layer to form reflecting layer 3. As the results, an uniform reflecting coating layer having a thickness of more than 1 mm can easily be obtained.

The coating layer produced by the combination of said fabric and specific paint has the following excellent characteristics.

1. It has excellent optical characteristics such as reflectance and diffusibility comparable to those of MgO smoked surface. It has a spectral reflectance to 400 – 700 m$\mu$ wavelength which is equivalent to that of fresh MgO smoked surface. Especially, with the conventional spray coated surface, the reflectance is conspicuously lowered in a wavelength of 200 – 400 m$\mu$, while the coating layer of the present invention is effective at near ultraviolet region.

2. A fabric is used as the medium and hence, a good adhesiveness can be obtained. The paint is firmly adhered to the fabric to obtain extremely high mechanical strength of the coating layer. Furthermore, the coating layer has no brittleness as does the MgO smoked surface or spray coated surface. Moreover, it has stable physical properties such as shock resistance and resistance to change of temperature.

3. Since the spray coating is carried out only one time, dispersion of paint is extremely reduced and the trouble of dusts is solved. Therefore, the present method is excellent in environmental sanitation and furthermore is economical.

4. As compared with the smoking method or spray coating method, the present method has no limitations in shape and size of the reflecting surface and the reflecting surface of any shapes and sizes can be produced.

5. As compared with the smoked surface and the spray coated surface, the present reflecting surface undergoes less deterioration with lapse of time and has a life more than 3 times longer than the conventional surfaces. Even when the coating layer is stained with dusts, etc., a fresh reflecting surface can always be reproduced only by slightly polishing the surface layer and carrying out spray coating only one time.

Next, the specific order of the steps of the present coating method is shown below.

1. Degreasing and rust proofing treatments

The surface to be coated is previously subjected to pretreatments such as degreasing and washing and then to rust proofing treatment.

In this case, if even a slight amount of oil, rust, etc. remains on the surface to be coated, they cause deterioration and later separation. Therefore, they must be completely removed. Special attention should be given to pin holes of moldings, the welded parts or cut parts of metal, etc.

2. Under coating and bonding of fabric

In general, kind of paints for under coating are charged depending upon kind of the surface to be coated. When the surface is metal or non-ferrous metal, a low temperature drying type epoxy resin paint is effective. This paint is not influenced by the material of base, is excellent in rust resistance and chemical resistance and has good adhesiveness to an aqueous finish paint. In case of using such resin paint as the undercoat paint, it is brush coated and simultaneously a fabric (including a net) can be bonded to the coating layer immediately before polymerization of the paint by the strong adhesiveness of the paint. In this case, no special adhesive is required, but an adhesive besides the undercoat paint may be used to obtain similar result.

3. Finish painting

Compositions of the finish paint are shown below.

The composition ratios were experimentally obtained from adhesiveness to the fabric, reflective characteristic of the surface of the coating layer after hardened, workability in production of a polishing putty etc. (The ratios in the following table is by weight.)

| Materials | Pigment | Film forming material | Solvent | Number of painting |
|---|---|---|---|---|
| Paint layers | Barium sulfate | Polyvinyl alcohol or C.M.C. | Distilled water | |
| 1 | 100 | 0.1 – 8 | 20 – 80 | 1 – 5 |
| 2 | 100 | 0 – 2 | 200 – 500 | 1 – 3 |

The second layer is a spray paint.

Selection of the materials is very important in preparation of the paint. Especially, quality of the pigment directly dominates the reflectance of the coating layers. Therefore, it is at least desirable to previously examine the reflective characteristics of the pigment itself and select a purified pigment in which no colorable impurities such as Fe, Cu, etc. are incorporated.

As the film forming material, polyvinyl alcohol (P.V.A.) is suitable, but carboxymethyl cellulose (C.M.C) may be substituted therefor or a mixture of the two may be used.

Preparation of the paint is carried out by previously dipping a given amount of polyvinyl alcohol in distilled water for 2 – 3 hours to swell the polyvinyl alcohol and thereafter dissolving it by heating for about 20 – 40 minutes at a temperature of higher than 80°C. In case of C.M.C., direct agitation at a temperature of 50° – 60°C results in dissolution of C.M.C. Barium sulfate is added to the resultant solution of binder and they are well mixed with a mixer such as roll mixer. Then, the mixture is filtered with a filter of 100 meshes to obtain a purified white putty. In this case, if the surface to be painted is a smooth or spherical surface, the amount of distilled water should be as small as possible and if the base to be coated is in a rod form, it is necessary to somewhat increase the amount of distilled water.

Coating

The putty is coated on a fabric with a simple spatula suitable to the shape and the size of the surface to be coated. Firstly, the putty is coated in a thickness of about 0.5 – 1 mm by one coating with care not to cause entrance of air into between putty and the fabric. If the putty is thickly coated at a time, inner part is dried with difficulty to cause formation of cracks and separation of the layers later. Therefore, coating is repeated in several times in such a manner that after one coating, the layer is necessarily dried and the coating is again effected. If a thickness of the coat is required to be more than 5 mm, a cheese cloth and the like may be further inserted to form a strong coating layer.

Regarding the drying, drying at normal temperature is preferred, but a forced drying may be employed at a surface temperature of up to 70°C.

Finishing

After a coating layer of the desired thickness is obtained and sufficiently dried, the surface thereof is lightly polished with a sand paper to make the surface smooth. In order to increase diffusibility, a paint having the compositions as shown in 2 in said Table is uniformly sprayed to the coating layer to obtain a uniform white reflecting surface.

What is claimed is:

1. A method for producing on a base plate a mechanically strong reflecting surface having optical reflectance and diffusibility characteristics comparable to those of an MgO smoked surface, said process comprising:
   1. cleansing the surface of said base plate to remove rust, grease, oil and the like contaminants therefrom,
   2. coating the cleansed surface produced thereby with an epoxy resin paint,
   3. bonding a fabric to the epoxy resin layer,
   4. coating the fabric with a first paint having a putty-like consistency and containing barium sulfate, water and at least one of polyvinyl alcohol and carboxy-methyl cellulose to form a reflecting layer, and
   5. polishing said reflecting layer to render its surface smooth.

2. A method according to claim 1, further comprising spray coating the polished surface with a second paint containing barium sulfate, water and at least one of polyvinyl alcohol and carboxy-methyl cellulose.

3. A method according to claim 1, wherein said first paint comprises 100 parts by weight barium sulfate, 20 to 80 parts by weight water and 0.1 to 8 parts by weight of at least one of polyvinyl alcohol and carboxy-methyl cellulose.

4. A method according to claim 3 further comprising spray coating the polished surface with a paint containing 100 parts by weight barium sulfate, 200 to 500 parts by weight water and 0 to 2 parts by weight of at least one of polyvinyl alcohol and carboxy-methyl cellulose.

5. A method according to claim 2, wherein said second paint contains 100 parts by weight barium sulfate, 200 to 500 parts by weight water and 2 parts by weight of at least one of polyvinyl alcohol and carboxy-methyl cellulose.

6. A method according to claim 4 wherein said base plate is a metal.

7. A method according to claim 6, wherein said metal is a non-ferrous metal.

8. A method according to claim 4, wherein said fabric is bonded to said epoxy resin layer by means of an adhesive.

9. A method according to claim 4, wherein said fabric is bonded to said epoxy resin layer without an adhesive.

10. A method according to claim 1, wherein the barium sulfate pigment is purified and free of colorable impurities.

11. A method according to claim 1, wherein said first paint is applied to the fabric in a plurality of layers, each layer having a thickness of about 0.5 to 1 mm.

12. A method according to claim 4, wherein said first paint is applied to said fabric in one to five layers, each layer having a thickness of 0.5 to about 1 mm.

13. A method according to claim 1, wherein said first paint is dried at ambiant temperatures.

14. A method according to claim 1, wherein said first paint is forced dried at a temperature up to about 70°C.

15. A method according to claim 1, wherein polishing is accomplished by rubbing an abrasive sheet material over said reflecting layer.

16. A method according to claim 15, wherein said abrasive sheet material is sand paper.

17. A method according to claim 3, further comprising spray coating the polished surface with from one to three layers of a second paint containing 100 parts by weight barium sulfate, 200 to 500 parts by weight water, and 0 to 2 parts by weight of at least one of polyvinyl alcohol and carboxy-methyl cellulose.

18. A method according to claim 1, wherein said water is distilled water.

19. The method for producing a mechanically strong reflecting surface having optical reflectance and diffusibility characteristics comparable to those of an MgO smoked surface on a metallic base plate comprising:
1. cleansing the surface of said base plate to be coated to remove rust, grease and oil therefrom,
2. coating the cleansed portion of said base plate with an epoxy resin paint,
3. bonding a fabric to said epoxy resin by embedding said fabric in the epoxy resin before it polymerizes completely,
4. coating said fabric with a putty-like paint consisting essentially of 100 parts by weight barium sulfate, 20 to 80 parts by weight water and 0.1 to 8 parts by weight of a binder selected from polyvinyl alcohol and carboxy-methyl cellulose to form a reflecting layer, and
5. polishing said reflecting layer to render it smooth.

20. A method according to claim 27 further comprising spray coating the polished reflecting layer with a second paint comprising 100 parts by weight barium sulfate, 200 to 500 parts by weight water and 0 to 2 parts by weight of at least one of polyvinyl alcohol and carboxy-methyl cellulose.

* * * * *